(12) United States Patent
Nakanishi et al.

(10) Patent No.: US 9,149,540 B2
(45) Date of Patent: Oct. 6, 2015

(54) POLYMER CONJUGATE OF FOLIC ACID OR FOLIC ACID DERIVATIVE

(75) Inventors: Takeshi Nakanishi, Tokyo (JP); Kazuhisa Hara, Tokyo (JP); Chieko Seno, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/991,041

(22) PCT Filed: Apr. 28, 2009

(86) PCT No.: PCT/JP2009/058325
§ 371 (c)(1),
(2), (4) Date: Jan. 24, 2011

(87) PCT Pub. No.: WO2009/136572
PCT Pub. Date: Nov. 12, 2009

(65) Prior Publication Data
US 2011/0294980 A1 Dec. 1, 2011

(30) Foreign Application Priority Data
May 8, 2008 (JP) .................................. 2008-122233

(51) Int. Cl.
A61K 47/48 (2006.01)
A61K 47/34 (2006.01)
A61K 31/785 (2006.01)
C08G 69/10 (2006.01)
C08G 69/40 (2006.01)
C08G 69/48 (2006.01)

(52) U.S. Cl.
CPC ......... *A61K 47/48315* (2013.01); *A61K 31/785* (2013.01); *A61K 47/34* (2013.01); *A61K 47/48215* (2013.01); *C08G 69/10* (2013.01); *C08G 69/40* (2013.01); *C08G 69/48* (2013.01)

(58) Field of Classification Search
None
See application file for complete search history.

(56) References Cited

U.S. PATENT DOCUMENTS

| | | | |
|---|---|---|---|
| 3,979,449 A | 9/1976 | Hirsbrunner et al. | |
| 4,734,512 A | 3/1988 | Kaneko et al. | |
| 4,892,733 A | 1/1990 | Bichon et al. | |
| 5,037,883 A | 8/1991 | Kopecek et al. | |
| 5,182,203 A * | 1/1993 | Ebersole et al. | 435/196 |
| 5,412,072 A | 5/1995 | Sakurai et al. | |
| 5,438,072 A | 8/1995 | Bobee | |
| 5,510,103 A | 4/1996 | Yokoyama et al. | |
| 5,552,517 A | 9/1996 | Martin | |
| 5,571,889 A | 11/1996 | Katoh et al. | |
| 5,614,549 A | 3/1997 | Greenwald et al. | |
| 5,639,832 A | 6/1997 | Kroner et al. | |
| 5,693,751 A * | 12/1997 | Sakurai et al. | 530/322 |
| 5,877,205 A | 3/1999 | Andersson | |
| 5,985,548 A * | 11/1999 | Collier et al. | 435/6.12 |
| 6,025,385 A | 2/2000 | Shimizu et al. | |
| 6,153,655 A | 11/2000 | Martinez et al. | |
| 6,262,107 B1 | 7/2001 | Li et al. | |
| 6,322,817 B1 | 11/2001 | Maitra et al. | |
| 6,376,470 B1 | 4/2002 | Greenwald et al. | |
| 6,410,731 B2 | 6/2002 | Curran et al. | |
| 6,458,347 B1 | 10/2002 | Sugawara et al. | |
| 6,573,284 B1 * | 6/2003 | Riley et al. | 514/346 |
| 6,596,757 B1 | 7/2003 | Chari et al. | |
| 6,713,454 B1 | 3/2004 | Ekwuribe et al. | |
| 6,720,304 B1 * | 4/2004 | Sinn et al. | 514/15.2 |
| 6,720,306 B2 | 4/2004 | Greenwald et al. | |
| 6,858,582 B2 * | 2/2005 | Yatvin et al. | 424/491 |
| 7,138,490 B2 | 11/2006 | Nakanishi et al. | |
| 7,176,185 B2 * | 2/2007 | Hilfinger et al. | 530/331 |

(Continued)

FOREIGN PATENT DOCUMENTS

CA 2383240 A1 3/2001
CA 2334615 A1 8/2001

(Continued)

OTHER PUBLICATIONS

Colloids and Surfaces B: Biointerfaces V 16 (1999) pp. 217-226, "Micelle-like structures of poly(ethyleneoxide)-block-poly(2-hydroxyethyl aspartamide)-methotrexate conjugates", Li, et al.

(Continued)

*Primary Examiner* — Michael G. Hartley
*Assistant Examiner* — Lance Rider
(74) *Attorney, Agent, or Firm* — Nields, Lemack & Frame, LLC

(57) ABSTRACT

Disclosed is a polymer conjugate of folic acid or a folic acid derivative, wherein an amide bond is not used. The compound has chemical stability and adequate drug release rate in the living organism. Specifically disclosed is a polymer conjugate of folic acid or a folic acid derivative, wherein a substituent represented by formula (I) is bonded to a carboxy group of a block copolymer which is composed of a polyethylene glycol and a polymer having a carboxy group in a side chain, or a pharmacologically acceptable salt thereof.

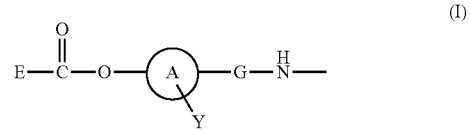

[In the formula, A represents a monocyclic or fused aromatic group; G represents an optionally substituted (C1-C6) alkylene group; Y represents a hydrogen atom or a substituent; and E represents a residue of folic acid or a folic acid derivative.]

6 Claims, 2 Drawing Sheets

(56) References Cited

U.S. PATENT DOCUMENTS

| | | |
|---|---|---|
| 7,495,099 B2 | 2/2009 | Kitagawa et al. |
| 7,700,709 B2 | 4/2010 | Masuda et al. |
| 7,820,759 B2 | 10/2010 | Shimizu et al. |
| 8,188,222 B2 | 5/2012 | Yamamoto et al. |
| 8,323,669 B2 | 12/2012 | Kitagawa et al. |
| 8,334,364 B2 | 12/2012 | Yamamoto et al. |
| 8,703,878 B2 | 4/2014 | Kitagawa et al. |
| 8,808,749 B2 | 8/2014 | Kitagawa et al. |
| 8,920,788 B2 | 12/2014 | Kitagawa et al. |
| 8,940,332 B2 | 1/2015 | Kitagawa et al. |
| 9,018,323 B2 | 4/2015 | Yamamoto et al. |
| 2001/0003779 A1 | 6/2001 | Curran et al. |
| 2001/0014354 A1 | 8/2001 | Yokoyama et al. |
| 2001/0041189 A1 | 11/2001 | Xu |
| 2002/0009426 A1 | 1/2002 | Greenwald et al. |
| 2002/0016285 A1 | 2/2002 | Bhatt et al. |
| 2002/0099013 A1 | 7/2002 | Piccariello et al. |
| 2002/0119951 A1 | 8/2002 | Seyedi et al. |
| 2002/0161062 A1 | 10/2002 | Biermann et al. |
| 2002/0183259 A1 | 12/2002 | Choe et al. |
| 2003/0032593 A1 | 2/2003 | Wender et al. |
| 2003/0054977 A1 | 3/2003 | Kumar et al. |
| 2003/0149003 A1 | 8/2003 | Chaplin et al. |
| 2005/0054026 A1 | 3/2005 | Atsushi et al. |
| 2005/0119193 A1* | 6/2005 | Motoyama ............ 514/25 |
| 2005/0147617 A1 | 7/2005 | Ji et al. |
| 2005/0171036 A1 | 8/2005 | Arakawa et al. |
| 2006/0009622 A1 | 1/2006 | Fuselier et al. |
| 2006/0057219 A1 | 3/2006 | Nagasaki et al. |
| 2006/0067910 A1 | 3/2006 | Kitagawa et al. |
| 2006/0099265 A1 | 5/2006 | Shimizu et al. |
| 2006/0233883 A1 | 10/2006 | Ishihara et al. |
| 2006/0258569 A1* | 11/2006 | McTavish ............ 514/8 |
| 2007/0004674 A1 | 1/2007 | Shiotsu et al. |
| 2007/0196497 A1 | 8/2007 | Pouliquen et al. |
| 2008/0113028 A1 | 5/2008 | Shimizu et al. |
| 2008/0145432 A1 | 6/2008 | Kakizawa et al. |
| 2008/0221062 A1 | 9/2008 | Miyamoto et al. |
| 2008/0269218 A1 | 10/2008 | Kuramochi et al. |
| 2008/0280937 A1 | 11/2008 | Leamon et al. |
| 2009/0012252 A1 | 1/2009 | Masuda et al. |
| 2009/0156742 A1 | 6/2009 | Shimizu et al. |
| 2009/0162313 A1 | 6/2009 | Kitagawa et al. |
| 2009/0239782 A1 | 9/2009 | Nakamura et al. |
| 2009/0275732 A1 | 11/2009 | Hirotsu et al. |
| 2009/0281300 A1 | 11/2009 | Yamamoto et al. |
| 2010/0004403 A1 | 1/2010 | Kitagawa et al. |
| 2010/0029849 A1 | 2/2010 | Yamamoto et al. |
| 2010/0234537 A1* | 9/2010 | Kitagawa et al. ........... 525/420 |
| 2010/0292414 A1 | 11/2010 | Kitagawa et al. |
| 2011/0136990 A1 | 6/2011 | Harada et al. |
| 2011/0201754 A1 | 8/2011 | Kitagawa et al. |
| 2012/0116051 A1 | 5/2012 | Kitagawa et al. |
| 2013/0331517 A1 | 12/2013 | Yamamoto et al. |
| 2014/0024703 A1 | 1/2014 | Shimizu et al. |
| 2014/0142167 A1 | 5/2014 | Shimizu et al. |
| 2014/0288244 A1 | 9/2014 | Yamamoto et al. |
| 2015/0011715 A1 | 1/2015 | Nakamura et al. |

FOREIGN PATENT DOCUMENTS

| | | | |
|---|---|---|---|
| CN | 1307866 A | 8/2001 | |
| CN | 1708540 A | 12/2005 | |
| CN | 1800238 A | 7/2006 | |
| EP | 0397307 A2 | 11/1990 | |
| EP | 0583955 A2 | 2/1994 | |
| EP | 0757049 A1 | 2/1997 | |
| EP | 1127570 A2 | 8/2001 | |
| EP | 1580216 A1 | 9/2005 | |
| EP | 1604687 A1 | 12/2005 | |
| EP | 1792927 A1 | 6/2007 | |
| EP | 1857446 A1 | 11/2007 | |
| EP | 2258397 A1 | 12/2010 | |
| JP | 61-243026 A | 10/1986 | |
| JP | 62-96088 A | 5/1987 | |
| JP | 62-145093 A | 6/1987 | |
| JP | 63-10789 A | 1/1988 | |
| JP | 63-23884 A | 2/1988 | |
| JP | 63-502037 A | 8/1988 | |
| JP | 64-61422 A | 3/1989 | |
| JP | 64-61423 A | 3/1989 | |
| JP | 2-300133 A | 12/1990 | |
| JP | 5-955 A | 1/1993 | |
| JP | 5-117385 A | 5/1993 | |
| JP | 6-107565 A | 4/1994 | |
| JP | 6-206815 A | 7/1994 | |
| JP | 6-206830 A | 7/1994 | |
| JP | 6-206832 A | 7/1994 | |
| JP | 6-329085 A | 11/1994 | |
| JP | 8-48766 A | 2/1996 | |
| JP | 8-503689 H | 4/1996 | |
| JP | 8-507558 A | 8/1996 | |
| JP | 8-310970 A | 11/1996 | |
| JP | 2694923 B2 | 12/1997 | |
| JP | 10-513187 H | 12/1998 | |
| JP | 11-335267 A | 12/1999 | |
| JP | 2000-515132 A | 11/2000 | |
| JP | 2000-516948 A | 12/2000 | |
| JP | 2000-517304 A | 12/2000 | |
| JP | 2001-226294 A | 8/2001 | |
| JP | 2002-69184 A | 3/2002 | |
| JP | 2002-508400 A | 3/2002 | |
| JP | 3268913 B2 | 3/2002 | |
| JP | 2002-512265 A | 4/2002 | |
| JP | 3310000 B2 | 7/2002 | |
| JP | 2003-509385 A | 3/2003 | |
| JP | 2003-509386 A | 3/2003 | |
| JP | 2003-511349 A | 3/2003 | |
| JP | 2003-511423 A | 3/2003 | |
| JP | 2003-524028 A | 8/2003 | |
| JP | 2003-525238 A | 8/2003 | |
| JP | 2003-527443 A | 9/2003 | |
| JP | 2003-342167 A | 12/2003 | |
| JP | 2003-342168 A | 12/2003 | |
| JP | 2003-342269 A | 12/2003 | |
| JP | 2004-530736 A | 10/2004 | |
| JP | 2004-532289 A | 10/2004 | |
| JP | 2005-507912 A | 3/2005 | |
| JP | 2005-508832 A | 4/2005 | |
| JP | 2005-517675 A | 6/2005 | |
| JP | 2005-519122 A | 6/2005 | |
| JP | 2005-533026 A | 11/2005 | |
| JP | 2006-510627 A | 3/2006 | |
| JP | 2006-511571 A | 4/2006 | |
| JP | 2006-517572 A | 7/2006 | |
| JP | 2006-521367 A | 9/2006 | |
| JP | 2006-524673 A | 11/2006 | |
| JP | 2007-511586 A | 5/2007 | |
| JP | 2007-191643 A | 8/2007 | |
| WO | 93/24476 A | 12/1993 | |
| WO | 96/23794 A | 8/1996 | |
| WO | 97/38727 A | 10/1997 | |
| WO | 98/02426 A | 1/1998 | |
| WO | 98/07713 A | 2/1998 | |
| WO | 98/08489 A1 | 3/1998 | |
| WO | 99/30727 A1 | 6/1999 | |
| WO | 99/53951 A | 10/1999 | |
| WO | 01/19361 A | 3/2001 | |
| WO | 01/19406 A2 | 3/2001 | |
| WO | 01/19407 A2 | 3/2001 | |
| WO | 01/26693 A | 4/2001 | |
| WO | 01/64198 A2 | 9/2001 | |
| WO | 01/70275 A2 | 9/2001 | |
| WO | 01/92584 A1 | 12/2001 | |
| WO | 02/06279 A1 | 1/2002 | |
| WO | 02/065986 A2 | 8/2002 | |
| WO | 02/065988 A2 | 8/2002 | |
| WO | 02/066066 A1 | 8/2002 | |
| WO | 03/000771 A1 | 1/2003 | |
| WO | 03/035008 A2 | 5/2003 | |
| WO | 03/055860 A1 | 7/2003 | |
| WO | 2004/039869 A1 | 5/2004 | |
| WO | 2004/050087 A1 | 6/2004 | |

(56) References Cited

FOREIGN PATENT DOCUMENTS

| | | |
|---|---|---|
| WO | 2004/056782 A1 | 7/2004 |
| WO | 2004/072051 A1 | 8/2004 |
| WO | 2004/082718 A1 | 9/2004 |
| WO | 2004/096212 A1 | 11/2004 |
| WO | 2005/000300 A1 | 1/2005 |
| WO | 2005/018674 A1 | 3/2005 |
| WO | 2005/066214 A1 | 7/2005 |
| WO | 2006/033296 A1 | 3/2006 |
| WO | 2006/055670 A2 | 5/2006 |
| WO | 2006/055760 A1 | 5/2006 |
| WO | 2006/095668 A1 | 9/2006 |
| WO | 2006/095783 A1 | 9/2006 |
| WO | 2006/101052 A1 | 9/2006 |
| WO | 2006/115293 A1 | 11/2006 |
| WO | 2006/120914 A | 11/2006 |
| WO | 2007/022493 A2 | 2/2007 |
| WO | 2007/080898 A1 | 7/2007 |
| WO | 2007/111211 A1 | 10/2007 |
| WO | 2007/135910 A1 | 11/2007 |
| WO | 2008/010463 A1 | 1/2008 |
| WO | 2008/041610 A1 | 4/2008 |
| WO | 2008/056596 A1 | 5/2008 |
| WO | 2008/056654 A1 | 5/2008 |
| WO | 2009/041570 A1 | 4/2009 |
| WO | 2009/116509 A1 | 9/2009 |
| WO | 2009/142326 A1 | 11/2009 |
| WO | 2010/131675 A1 | 11/2010 |

OTHER PUBLICATIONS

Pharmaceutical Research, V. 17, No. 5 (2000) pp. 607-611, "Methotrexate Esters of Poly(EthyleneOxide)-Block-Poly(2-Hydroxyethyl-L-Aspartamide). Part I: Effects of the Level of Methotrexate Conjugation on the Stability of Micelles and on Drug Release", Li, et al.
International Search Report dated Jul. 21, 2009.
Taiwanese Communication, with English translation, dated Dec. 14, 2011 in co-pending Taiwanese Application No. 094132581.
International Search Report dated Aug. 10, 2010 in co-pending PCT application No. PCT/JP2010/058034.
Final Rejection dated Feb. 16, 2012 in co-pending U.S. Appl. No. 12/226,962.
Office Action dated Feb. 21, 2012 in co-pending U.S. Appl. No. 12/312,009.
Notice of Allowance dated Mar. 1, 2012 in co-pending U.S. Appl. No. 12/312,157.
European Communication mailed Jan. 27, 2012 in co-pending European Patent Application No. 0781039.8.
Antimicrobial Agents and Chemotherapy, vol. 2, No. 5, Nov. 1972, pp. 395-401, XP 55016709, ISSN: 0066-4804, "Antiviral Action of Camptothecin", Horwitz, et al.
Office Action mailed Apr. 6, 2012 in co-pending U.S. Appl. No. 12/225,230.
Miscellaneous Communication mailed Mar. 19, 2012 in co-pending U.S. Appl. No. 12/312,157.
Office Action mailed Apr. 25, 2012 in co-pending U.S. Appl. No. 12/678,620.
Office Action—Restriction—mailed Apr. 27, 2012 in co-pending U.S. Appl. No. 12/922,747.
International Search Report dated Jan. 29, 2008 in co-pending international patent application No. PCT/JP2007/071305.
International Search Report dated Jan. 29, 2008 in co-pending international patent application No. PCT/JP2007/071532.
International Search Report dated Dec. 9, 2008 in co-pending international patent application No. PCT/JP2008/067413.
Office Action dated Jan. 21, 2009 in co-pending U.S. Appl. No. 10/548,998.
Office Action dated Apr. 17, 2009 in co-pending U.S. Appl. No. 10/548,998.
Office Action dated Jul. 10, 2009 in co-pending U.S. Appl. No. 10/548,998.
Final Rejection dated Mar. 4, 2010 in co-pending U.S. Appl. No. 10/548,998.
Office Action dated Aug. 24, 2010 in co-pending U.S. Appl. No. 11/662,834.
Office Action dated Nov. 12, 2010 in co-pending U.S. Appl. No. 11/662,834.
Final Rejection dated Jun. 8, 2011 in co-pending U.S. Appl. No. 11/662,834.
Office Action dated Jun. 16, 2011 in co-pending U.S. Appl. No. 12/225,230.
Office Action dated Sep. 9, 2011 in co-pending U.S. Appl. No. 12/226,962.
Office Action dated Jul. 21, 2010 in abandoned U.S. Appl. No. 12/309,061.
Final Rejection dated Feb. 28, 2011 in abandoned U.S. Appl. No. 12/309,061.
Office Action dated Apr. 4, 2011 in co-pending U.S. Appl. No. 12/311,086.
Final Rejection dated Jul. 27, 2011 in co-pending U.S. Appl. No. 12/311,086.
Course for Universities, Third Edition, Revised and supplemented, "Visshaja Shkola" Publishing House, 1981, 656 pages, see p. 265, "High-Molecular Weight Compounds", SHUR.
6001 Chemical Abstracts, American Chemical Society, US, vol. 132, No. 2, Oct. 1, 2000, XP-002168038, 1 page abstract, "Polymer Micelle Compositions Containing Poorly Water-Soluble Drugs and their Preparation", Ichiro, et al.
Merriam-Webster's Collegiate Dictionary—11th Edition, 2004, 22 pages.
J. Org. Chem 2001, 66, 8135-8138, "Novel Syntheses of Cis and Trans Isomers of Combretastatin A-4", Gaukroger, et al.
Anti Cancer Drug Design, vol. 14, No. 6, Dec. 1999, ISSN 0266-9536, pp. 539-548, "Synthesis and antitumor activities of amino acid prodrugs of amino-combretastatins", Ohsumi, et al.
Journal of Pharmaceutical Sciences, vol. 92, No. 7, Jul. 2003, pp. 1343-1355, "MiniReview-Amphiphilic Block Copolymers for Drug Delivery", Adams, et al.
Chemistry and Biology, vol. 11, 787-797, Jun. 2004, "Targeting Wide-Range Oncogenic Transformation via PU24FCI, a Specific Inhibitor of Tumor Hsp90", Vilenchik, et al.
Trends in Molecular Medicine, vol. 8, No. 4, (Supp.) 2002, p. S55-S61, "Hsp90 Inhibitors as Novel Cancer Chemotherapeutic Agents", Neckers, et al.
Current Cancer Drug Targets, 2003, vol. 3, 385-390, "The Clinical Applications of Heat Shock Protein Inhibitors in Cancer—Present and Future", Banerji, et al.
Cancer Science, Feb. 2004, V. 95, No. 2, 105-111, "Antitumor Activity of Sugar-Modified Cytosine Nucleosides", Matsuda, et al.
Cancer Research vol. 44, 25-30, Jan. 1984, "Antitumor Activity of 1-B-D-Arabinofuranosylcytosine Conjugated with Polyglutamic Acid and its Derivative", Kato, et al.
Journal of Controlled Release vol. 79 (2002), 55-70, "Anticancer Drug Delivery Systems: Multi-Loaded N4-acyl poly (ethylene glycol) prodrugs of ara-C. II. Efficacy in ascites and solid tumors", Choe, et al.
J. of Pharmacokinetics and BioPharmaceutics, vol. 23, No. 4, 1995, pp. 397-406, "In Vivo Pharmacokinetic Study for the Assessment of Poly(L-Aspartic Acid) as a Drug Carrier for Colon-Specific Drug Delivery", Leopold, et al.
Advanced Drug Delivery Reviews, vol. 20, (1996), 195-201, "Limethason as a lipid microsphere preparation: An Overview", Yokoyama, et al.
Journal of Peptide Science, vol. 3 (1997), 141-144, "Evaluation of Carbodiimides Using A Competition Method", Izdebski, et al.
Bioorganic & Medicinal Chemistry Letters, 2005, vol. 15, 3338-3343, "The identification, synthesis, protein crystal structure and in vitro biochemical evaluation of a new 3,4-diarylpyrazole class of Hsp90 inhibitors", Cheung, et al.
Molecular Cancer Therapeutics 2006, vol. 5, 1628-1637, "Preclinical pharmacokinetics and metabolism of a novel diaryl pyrazole resorcinol series of heat shock protein 90 inhibitors", Smith, et al.
Registry Entry for Registry No. 171009-07-07, which entered STN on Dec. 6, 1995, 3 pages.

(56) References Cited

OTHER PUBLICATIONS

Registry Entry for Registry No. 7689-03-4, which entered STN on Nov. 16, 1984, 3 pages.
Merriam Webster Online Dictionary entry for "Derivative", (http://www.merriam-webster.com/dictionary/derivative), last accessed Feb. 9, 2011, 3 pages.
Office Action dated Oct. 12, 2011 in co-pending U.S. Appl. No. 12/312,157.
International Search Report dated Dec. 24, 2003 in international patent application No. PCT/JP03/13838 (now USP 7,495,099).
Taiwanese Communication dated Nov. 30, 2006 in international patent application No. TW092130275 (now USP 7,495,099).
Russian Communication dated Apr. 20, 2007 in international patent application No. RU2005116309 now USP 7,495,099).
European Communication dated Sep. 25, 2008 in international patent application No. EP03769949.3 (now USP 7,495,099).
International Search Report dated May 11, 2004 in co-pending international patent application No. PCT/JP2004/003647.
Chinese Communicaton dated Oct. 20, 2006 in co-pending international patent application No. CN200480007329.5.
Russian Communication dated Jun. 27, 2007 in co-pending international patent application No. RU2005132309/04.
European Communication dated Feb. 17, 2009 in co-pending international patent application No. EP04721673.4.
Chinese Communication, with English translation, dated Apr. 17, 2009 in co-pending international patent application No. CN200480007329.5.
European Communication dated Jun. 5, 2009 in co-pending international patent application No. EP04721673.4.
Korean Communication dated Nov. 8, 2010 in co-pending international patent application No. 10-2005-7017245.
International Search Report dated Nov. 15, 2005 in co-pending international patent application No. PCT/JP2005/017127.
Taiwanese Communication dated Jul. 22, 2011 in co-pending Taiwanese patent application No. 094132581.
International Search Report dated Jul. 25, 2006 in international patent application No. PCT/JP2006/308826 (USP 7,700,709).
International Search Report dated May 15, 2007 in co-pending international patent application No. PCT/JP2007/055809.
International Search Report dated Aug. 21, 2007 in co-pending international patent application No. PCT/JP2007/060026.
European Communication dated Oct. 23, 2009 in co-pending international patent application No. EP07743461.1.
Chinese Communication dated Aug. 11, 2010 in co-pending international patent application No. CN2007800177809.
Russian Communication, with English translation, dated May 16, 2011 in co-pending international patent application No. RU2008149932/04.
International Search Report dated Oct. 16, 2007 in co-pending international patent application No. PCT/JP2007/063990.
Chinese Communication dated Nov. 10, 2010 in co-pending international patent application No. CN 200780027210.8.
International Search Report dated Jan. 8, 2008 in co-pending international patent application No. PCT/JP2007/068841.
Office Action mailed Oct. 25, 2011 in co-pending U.S. Appl. No. 12/312,009.
Final Rejection mailed Nov. 8, 2011 in co-pending U.S. Appl. No. 12/225,230.
Chinese Communication, with English translation, dated Sep. 23, 2011 in co-pending Chinese patent application No. 2007800177809.
Journal of Controlled Release, 2001, V. 74, No. 1-3, pp. 295-302, paragraph of "2. Structure of NK911", "Development of the polymer micelle carrier system for doxorubicin", Nakanishi, et al.
International Search Report mailed Jun. 23, 2009 in co-pending PCT application No. PCT/JP2009/055115.
Chinese Communicaton, with English translation, dated Aug. 31, 2011 in co-pending Chinese patent application No. 200980110087.5.
European Communication, dated Oct. 28, 2011 in co-pending European Patent Application No. EP 05783310.5.
Australian Communication, dated Oct. 28, 2011 in co-pending Australian Patent Application No. 2007252678.
Chinese Communication, with English translation, dated Oct. 10, 2011 in co-pending Chinese Patent Application No. 20880109404.7.
Office Action dated Dec. 15, 2011 in co-pending U.S. Appl. No. 11/662,834.
Final Rejection mailed Aug. 21, 2012 in co-pending U.S. Appl. No. 11/662,834.
Notice of Allowance mailed Aug. 28, 2012 in co-pending U.S. Appl. No. 12/225,230.
Notice of Allowance mailed Aug. 7, 2012 in co-pending U.S. Appl. No. 12/312,009.
Office Action mailed Jul. 30, 2012 in co-pending U.S. Appl. No. 12/922,747.
Final Rejection mailed Oct. 17, 2012 in co-pending U.S. Appl. No. 12/678,620.
Office Action—Restriction—mailed Jan. 29, 2013 in co-pending U.S. Appl. No. 13/319,175.
Chinese Communication, with English translation, mailed Dec. 31, 2013 in co-pending Chinese patent application No. CN 200980110087.5.
Japanese communication, with English translation, mailed Sep. 24, 2013 in co-pending Japanese patent application No. JP 2010-503871.
Office Action mailed Oct. 7, 2013 in co-pending U.S. Appl. No. 10/548,998.
Office Action mailed Sep. 6, 2013 in co-pending U.S. Appl. No. 12/922,747.
The Merck Index, Fourteenth Edition, 2006, p. 1-16, O'Neil, et al.
Japanese communication, with English translation, mailed Jul. 8, 2014 in co-pending Japanese patent application No. 2010-503871.
Office Action mailed Oct. 1, 2014 in co-pending U.S. Appl. No. 14/241,924.
Notice of Allowance mailed Oct. 8, 2014 in co-pending U.S. Appl. No. 12/922,747.
English translation of JP 6-206815 (Jul. 26, 1994), "Pharmaceutical Preparation Based on Block Copolymer-Anticancer Drug Complex", by Masayuki Yokoyama, et al., 24 pages, US Patent and Trademark Office, Aug. 2007, Translated by: FLS, Inc.
Office Action mailed Dec. 31, 2014 in co-pending U.S. Appl. No. 13/971,036.
Notice of Allowance mailed Jan. 28, 2015 in co-pending U.S. Appl. No. 13/884,413.
Final Rejection mailed Jan. 10, 2014 in co-pending U.S. Appl. No. 13/319,175.
Notice of Allowance mailed Jan. 16, 2014 in co-pending U.S. Appl. No. 12/678,620.
European communication dated Mar. 11, 2015 in co-pending European patent application No. 12830758.4.
Final Rejection mailed Mar. 4, 2015 in co-pending U.S. Appl. No. 11/662,834.
Final Rejection mailed Apr. 21, 2015 in co-pending U.S. Appl. No. 14/241,924.
International Search Report mailed Dec. 4, 2012 in co-pending PCT application No. PCT/JP2012/072160.
Written Opinion mailed Dec. 4, 2012 in co-pending PCT application No. PCT/JP2012/072160.
International Preliminary Report on Patentability mailed Mar. 20, 2014 in co-pending PCT application No. PCT/JP2012/072160.
Final Rejection mailed Apr. 7, 2014 in co-pending U.S. Appl. No. 12/922,747.
Notice of Allowance mailed May 15, 2014 in co-pending U.S. Appl. No. 13/319,175.
International Preliminary Report on Patentability, with English translation, issued Apr. 7, 2009 and Apr. 22, 2009 in co-pending PCT application No. PCT/JP2007/068841.
Japanese Communication, with English translation, mailed Mar. 26, 2013 in co-pending Japanese Patent Application No. 2008-537500.
Canadian Communication issued Jun. 26, 2013 in co-pending Canadian patent application No. CA 2,664,852.
Japanese Communication, with partial English translation, mailed May 14, 2013 in co-pending Japanese patent application No. JP 2009-534401.

(56) References Cited

OTHER PUBLICATIONS

European Communication mailed May 24, 2013 in co-pending European patent application No. 09722008.1.
Chinese Communication, with English translation, mailed Feb. 22, 2013 in co-pending Chinese Patent Application No. 201080021960.6.
International Search Report and Written Opinion mailed Jan. 24, 2012 in co-pending PCT application No. PCT/JP2011/076373.
Office Action mailed Apr. 18, 2013 in co-pending U.S. Appl. No. 12/311,086.
Final Rejection mailed Aug. 28, 2013 in co-pending U.S. Appl. No. 12/311,086.
Office Action mailed Jun. 12, 2013 in co-pending U.S. Appl. No. 13/319,175.
Advanced Drug Delivery Reviews, vol. 55, No. 2, Feb. 2003, pp. 217-250, "Effective drug delivery by PEGylated drug conjugates", Greenwald, et al.
Chinese communication, with English translation, mailed Jun. 17, 2014 in co-pending Chinese patent application no. 200980110087.5 (441P134).
Office Action mailed Aug. 25, 2014 in co-pending U.S. Appl. No. 11/662,834.
Notice of Allowance mailed Sep. 11, 2014 in co-pending U.S. Appl. No. 12/226,962.
Examiner's Answer to Appeal Brief mailed Jul. 29, 2014 in co-pending U.S. Appl. No. 12/311,086.
European communication dated Oct. 29, 2014 in corresponding European patent application No. 09742696.9.
Office Action mailed Nov. 24, 2014 in co-pending U.S. Appl. No. 14/497,703.
Final Rejection mailed Mar. 5, 2013 in co-pending U.S. Appl. No. 12/922,747.
Final Rejection mailed May 28, 2015 in co-pending U.S. Appl. No. 14/497,703.

* cited by examiner

POLYMER CONJUGATE OF FOLIC ACID OR FOLIC ACID DERIVATIVE

TECHNICAL FIELD

The present invention relates to a polymer conjugate of folic acid or a folic acid derivative, a method for producing the polymer conjugate, and use of the polymer conjugate.

BACKGROUND ART

Folic acid is one of water-soluble vitamins, and is a coenzyme necessary in the synthesis of amino acids or nucleic acids. Folic acid is converted to tetrahydrofolic acid by a reductase in the body, and then is further converted to be used in the synthesis of dTMP (deoxythymidine-1-phosphate) or purine. Folic acid derivatives include compounds that have a function of inhibiting the in vivo conversion of folic acid and thereby terminating cell division. A group of these compounds are called as folic acid antimetabolites, and methotrexate, which is a representative compound of the group, has long been used in the treatment of leukemia, sarcoma, stomach cancer and the like. Furthermore, methotrexate also has an immunomodulating action and thus serves as an essential drug for the chemotherapy of rheumatoid arthritis.

In addition, folic acid itself or a folic acid derivative such as leucovorin is also used as a drug for treating folic acid deficiency or neutralizing the toxicity of methotrexate.

As such, folic acid, or a folic acid derivative, for example, a folic acid antimetabolite which is represented by methotrexate, is a compound useful as a pharmaceutical product, and research on various derivatives is in progress for the purpose of improving the drug efficacy. Examples of these derivatives include aminopterin, pralatrexate, plevitrexed, edatrexate, pemetrexed, raltitrexed, lometrexol and the like, as shown below. The mode of action of these folic acid antimetabolites is mainly a dihydrofolate reductase inhibitory activity, but among the drugs newly developed, some even have a thymidylate synthetase inhibitory activity. Thus, there is a demand for more effective drugs, and development of those drugs is under way. For example, pemetrexed is characterized by inhibiting multiple enzymes involved in the folic acid metabolic system, and has been approved as a therapeutic drug for malignant pleural mesothelioma.

[Chemical Formula 1]

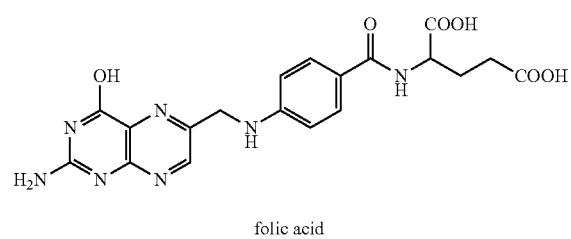

folic acid

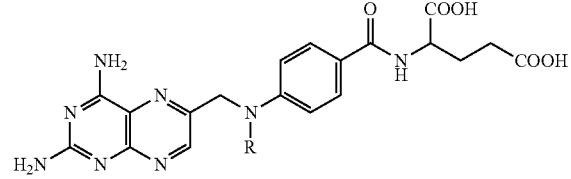

aminopterin; R = H
methotrexate; R = Me

-continued

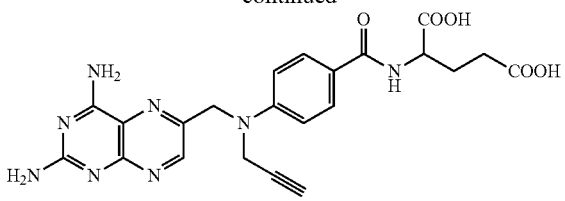

pralatrexate

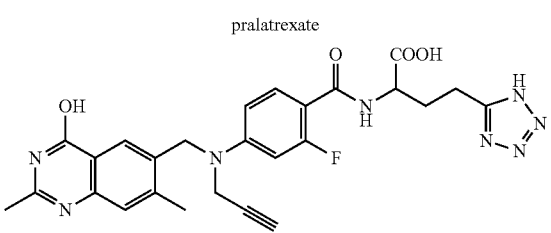

plevitrexed

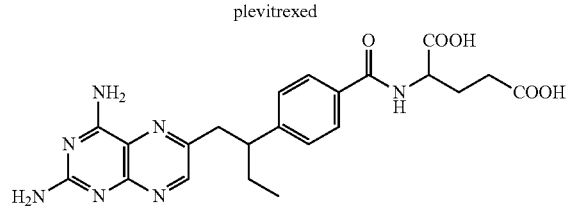

edatrexate

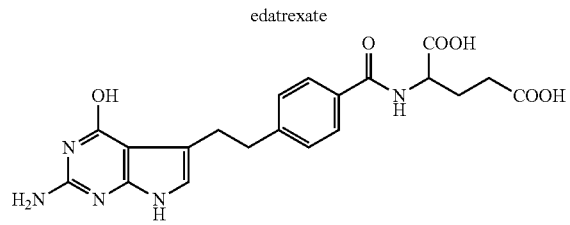

pemetrexed

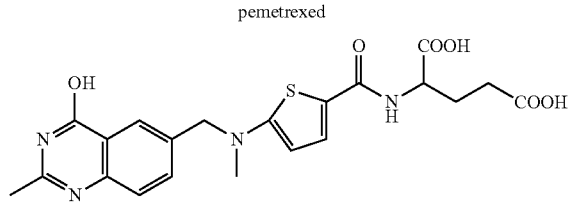

raltitrexed

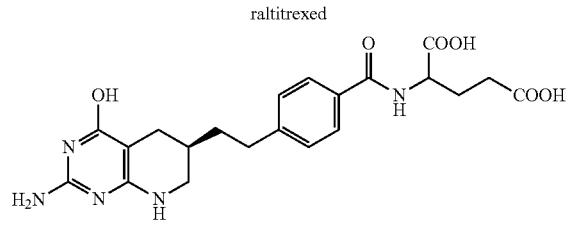

lometrexol

On the other hand, an experiment intended for the reduction of toxicity and enhancement of effects of low molecular weight drugs has been made as a part of the research on drug delivery systems (DDS). Various methods are available to achieve the object, for example, a drug may be bound to a polymer or may encapsulated in a nano-sized carrier. Regarding methotrexate, which is a compound representing folic acid derivatives, systems utilizing microspheres, dendrimers and micelles have been reported. However, none of the reports can be sufficiently satisfy the final purposes of the DDS research, that is, enhanced effects and reduced adverse side effects.

Patent Document 1 and Patent Document 3 describe water-soluble macromolecular pharmaceutical preparations containing, as a carrier, micelles formed by an amphiphilic polymer. Patent Document 1 describes, as an example of a hydrophobic segment, a polymer carrier having methotrexate bound thereto, but in this case, methotrexate and the amphiphilic polymer are linked via an amide bond. Patent Document 3 does not describe a polymer conjugate having folic acid or a folic acid derivative bound thereto.

Patent Document 2 reports that chemical stability and in vivo drug release efficiency can be simultaneously achieved by linking a polymer compound and a camptothecin compound via a phenyl ester bond. However, this method cannot be directly used for a carboxy group of a folic acid derivative (including folic acid itself), which is represented by methotrexate.

Furthermore, Non-Patent Document 1 and Non-Patent Document 2 describe polymer conjugates, which use a carboxy group of methotrexate to link methotrexate to an amphiphilic polymer via an alkyl ester bond. However, in this case, the release rate of drug is slow, and there arises a question on whether the effects of the drug would be exhibited. Furthermore, when the release of a drug from a polymer conjugate is dependent on the enzymes in vivo, there is a fear that the enzymatic activity, which varies between individuals, may cause variability in the drug release rate, and may consequently cause variability in the efficacy.

RELATED ART DOCUMENT

Patent Document

Patent Document 1: Japanese Patent Application Laid-Open (JP-A) No. 2-300133
Patent Document 2: International Publication No. WO 2004/039869
Patent Document 3: International Publication No. WO 2003/000771

Non-Patent Document

Non-Patent Document 1: "Colloid and Surface B: Biointerface", Vol. 16, pp. 217-226 (1999)
Non-Patent Document 2: "Pharmaceutical Research", Vol. 17, pp. 607-611 (2000)

DISCLOSURE OF THE INVENTION

Problem to be Solved by the Invention

The bond between the drug and the amphiphilic polymer used in Patent Document 1 is an amide bond, but the amide bond is chemically stable, so that when the polymer conjugate is administered in vivo, the release rate of the drug is quite slow and not practical.

In order to enhance the pharmacological effects by converting a drug into a polymer conjugate, it is necessary that the drug is released from the polymer conjugate at an appropriate rate, and simply binding the drug with a polymer compound is not sufficient. When the bonding between the drug and the polymer compound is weak, not only the polymer conjugate becomes so unstable that it is very difficult to obtain a drug preparation, but also the release of the drug occurs so rapidly that an improvement in the pharmacokinetics and the like resulting from the bonding of the drug to a polymer compound cannot be expected. Furthermore, if the bonding is excessively strong, even though the pharmacokinetics is improved, the drug is not released from the polymer conjugate, and the pharmacological effects can not be exhibited.

Thus, there is a demand for a compound which is a polymer conjugate of folic acid or a folic acid derivative that does not use an amide bond, and which has chemical stability and appropriate in vivo drug release efficiency.

Means for Solving the Problem

The inventors of the present invention made extensive efforts to solve the problems such as described above, and as a result, the inventors found a polymer conjugate in which a block copolymer composed of a polyethylene glycol and a polymer having a carboxylic acid in a side chain, is linked to folic acid or a folic acid derivative via a particular linker molecule. Thus, the inventors completed the present invention.

Specifically, the present invention relates to the following items (1) to (11).

(1) A polymer conjugate of folic acid or a folic acid derivative, or a pharmacologically acceptable salt thereof, which is a block copolymer comprising a polyethylene glycol and a polymer having a carboxy group in a side chain to which a substituent represented by the following formula (I) is linked:

[Chemical Formula 2]

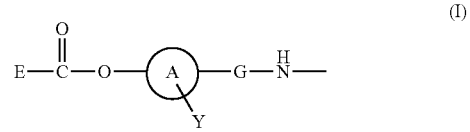

wherein A represents a monocyclic or fused aromatic group; G represents a (C1-C6) alkylene group which may be substituted; Y represents a hydrogen atom or a substituent; and E represents a residue of folic acid or a folic acid derivative.

(2) The polymer conjugate of folic acid or a folic acid derivative or a pharmacologically acceptable salt thereof according to the above item (1), wherein the polymer having a carboxy group in a side chain is a poly(acidic amino acid).

(3) The polymer conjugate of folic acid or a folic acid derivative or a pharmacologically acceptable salt thereof according to the above item (2), wherein the poly(acidic amino acid) is polyaspartic acid or polyglutamic acid.

(4) The polymer conjugate of folic acid or a folic acid derivative or a pharmacologically acceptable salt thereof according to any one of the above items (1) to (3), which is represented by the following formula (II):

[Chemical Formula 3]

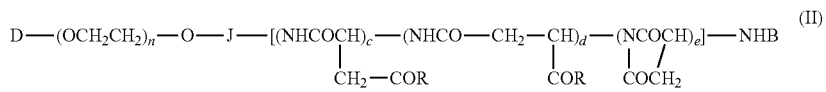

wherein D represents a hydrogen atom or a (C1-C6) alkyl group which may be substituted; a mean value of n is 5 to 11500; J represents a (C2-C6) alkylene group; a mean value of c+d+e is 3 to 200, while c+d represents an integer; R represents a hydroxy group or the substituent represented by the formula (I), whereas at least one of R in one molecule is the substituent represented by the formula (I); and B represents a hydrogen atom or a (C1-C6) acyl group.

(5) The polymer conjugate of folic acid or a folic acid derivative or a pharmacologically acceptable salt thereof according to the above item (4), wherein D represents an unsubstituted (C1-C6) alkyl group, a mean value of n is 50 to 1000, a mean value of c+d+e is 5 to 100, and B represents a (C1-C6) acyl group.

(6) The polymer conjugate of folic acid or a folic acid derivative or a pharmacologically acceptable salt thereof according to any one of the above items (1) to (5), wherein the substituent represented by the formula (I) is a substituent represented by the following formula (III):

[Chemical Formula 4]

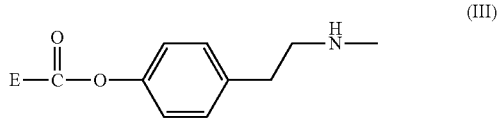

(III)

wherein E represents a residue of folic acid or a folic acid derivative.

(7) The polymer conjugate of folic acid or a folic acid derivative or a pharmacologically acceptable salt thereof according to any one of the above items (1) to (6), wherein the folic acid derivative is methotrexate.

(8) The polymer conjugate of folic acid or a folic acid derivative or a pharmacologically acceptable salt thereof according to any one of the above items (1) to (6), wherein the folic acid derivative is pemetrexed.

(9) An anticancer drug comprising, as an active ingredient, the polymer conjugate of folic acid or a folic acid derivative or a pharmacologically acceptable salt thereof according to any one of the above items (1) to (8).

(10) A therapeutic drug for inflammatory diseases comprising, as an active ingredient, the polymer conjugate of folic acid or a folic acid derivative or a pharmacologically acceptable salt thereof according to any one of the above items (1) to (8).

(11) A method for producing a polymer conjugate of folic acid or a folic acid derivative by linking folic acid or a folic acid derivative to the phenolic hydroxy group of a compound represented by formula (IV) via an ester bond; removing a protective group of an amino group; and subsequently producing an amide bond by dehydration-condensation of the resulting deprotection product and a carboxy group of a block copolymer composed of a polyethylene glycol and a polymer having a carboxy group in a side chain.

[Chemical Formula 5]

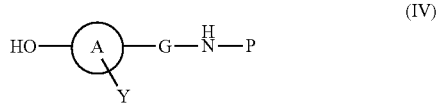

(IV)

wherein A represents a monocyclic or fused aromatic group; G represents a (C1-C6) alkylene group which may be substituted; P represents the protective group of the amino group; and Y represents a hydrogen atom or a substituent.

Effect of the Invention

In general, since a polymer compound is not constituted of a single molecule and there is a variance in the molecular weight or the composition of the polymer compounds, it is difficult to carry out a strict chemical analysis. Furthermore, since folic acid or a folic acid derivative has multiple amino groups and carboxy groups, there is multiple linkage forms. However, according to the present invention, separation and purification can be carried out after folic acid or the folic acid derivative is condensed with a linker molecule, and the condensation reaction between the compound thus obtained and a block copolymer proceeds relatively easily, so that the quality of the polymer conjugate of folic acid or a folic acid derivative obtainable in this way can be made consistent.

Furthermore, since the polymer conjugate of the present invention contains a drug and a linker molecule bound via a phenyl ester bond, practical chemical stability and excellent in vivo drug release efficiency can be simultaneously achieved, and enhancement of the pharmacological effects and reduction of adverse side effects can be made possible.

Furthermore, the rate of drug release from the polymer conjugate of folic acid or a folic acid derivative of the present invention can be controlled by changing the substituent of the linker moiety or selecting the carboxy group of the drug being bound. In addition, since mixing these polymer conjugates having different release rates also allows regulation of the drug release rate, the polymer conjugate of the present invention can be applied to a wider range of applications.

BEST MODE FOR CARRYING OUT THE INVENTION

Figure 1:
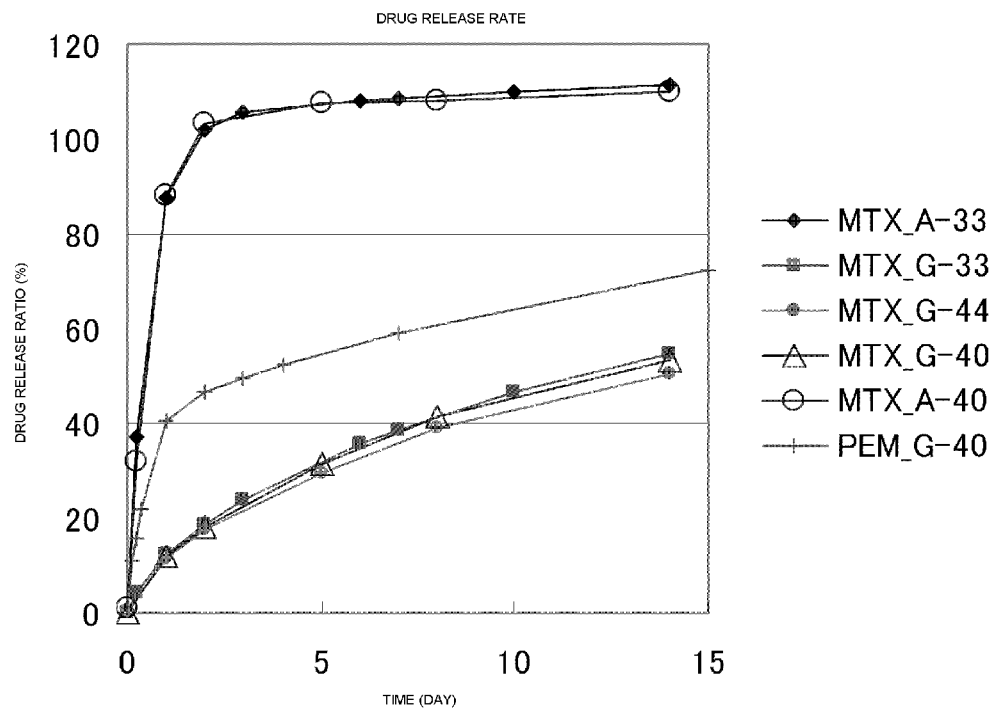
FIG. 1 is a diagram showing the drug release rate in the absence of a hydrolase in Test Example 1, as the ratio with respect to the total amount of drug bound to the polymer conjugate.

The present invention provides a polymer conjugate of folic acid or a folic acid derivative or a pharmacologically acceptable salt of thereof comprising a block copolymer composed of a polyethylene glycol and a polymer having a carboxy group in a side chain, and a substituent represented by the formula (I) which is linked to the carboxy group of the polymer [wherein A represents a monocyclic or fused aromatic group; G represents a (C1-C6) alkylene group which may be substituted; Y represents a hydrogen atom or a substituent; and E represents a residue of folic acid or a folic acid derivative].

The polyethylene glycol includes polyethylene glycols modified at both ends or at a single end as well, and the terminal modifying groups present at the two ends may be identical or different. The terminal modifying group may be a (C1-C6) alkyl group which may be substituted, and preferred examples include a methyl group, an ethyl group, an n-propyl group, an i-propyl group, an n-butyl group, an s-butyl group, a t-butyl group, a benzyl group, a dimethoxyethyl group, a diethoxyethyl group, an aminomethyl group, an aminoethyl group, a 3-aminopropyl group, and a 4-aminobutyl group.

The molecular weight of the polyethylene glycol moiety is usually about 300 to 500,000, preferably about 500 to 100,000, and more preferably about 1000 to 50,000. Here, the molecular weight according to the present invention is a peak top molecular weight measured by gel permeation chromatography (GPC method).

The polymer having a carboxy group in a side chain may be a polymer containing a constituent unit having a carboxy group in a side chain, and examples of the constituent unit having a carboxy group in a side chain include acrylic acid, methacrylic acid, malic acid, aspartic acid, and glutamic acid, while examples of the polymer having a carboxy group in a side chain include polyacrylic acid, polymethacrylic acid, polymalic acid, polyaspartic acid and polyglutamic acid. Among them, a poly(acidic amino acid) is preferred, and for example, polyaspartic acid or polyglutamic acid is preferred, while polyaspartic acid is particularly preferred.

The number of carboxy groups per molecule of the block copolymer according to the present invention is preferably about 3 to 200, and more preferably about 5 to 100.

The block copolymer according to the present invention may be a compound obtained by linking a polyethylene glycol having a functional group at an end with a polycarboxylic acid having a functional group at an end, or a compound obtainable by a polymerization reaction of an activated amino acid, in which polymerization is initiated by a polyethylene glycol having an amino group at an end, as described in Patent Document 1 or Patent Document 3.

In the formula (I), A represents a monocyclic or fused aromatic group and is not particularly limited. However, a (C6-C18) aromatic group that does not contain any heteroatom is preferred, and examples thereof include a phenyl group, a naphthyl group and an anthryl group. Among them, a phenyl group is particularly preferred. The positions of substitution of the phenolic hydroxy group and the aminoalkyl group are not particularly limited.

Y in the moiety A of the formula (I) represents a hydrogen atom or a substituent bonded to the monocyclic or fused aromatic group, and examples of the substituent include a (C1-C3) alkyl group such as a methyl group, an ethyl group or an isopropyl group; a (C1-C3) alkoxy group such as a methoxy group, an ethoxy group or a propoxy group; a halogen atom such as a chlorine atom or a bromine atom; a (C1-C3) acyl group such as a formyl group or an acetyl group; a nitro group, a cyano group, and a hydroxy group.

The strength of the bond between folic acid or the folic acid derivative and a linker molecule is greatly affected by the degree of acidity of the phenolic hydroxy group acquired when the linker molecule is cleaved. Thus, when the degree of acidity is changed by changing Y, the strength of the bond between folic acid or the folic acid derivative and the linker molecule also changes. For example, when A is a phenyl group, a cyano group, a nitro group, a halogen atom and the like, which are electron-withdrawing groups, are preferred in order to advance the release of folic acid or the folic acid derivative, and an alkyl group, and the like which are an electron-donating group, are preferred in order to delay the release of folic acid or the folic acid derivative. The number of substitution of Y is not particularly limited as long as substitution can be made.

When Y is a substituent, the position of substitution needs to be selected while its effect on the release rate is considered, but the position of substitution is not particularly limited.

In the formula (I), G represents a (C1-C6) alkylene group which may be substituted, and examples thereof include a methylene group, an ethylene group, a trimethylene group, a tetramethylene group, a methylethylene group, a dimethylethylene group, a methoxyethylene group, an ethoxyethylene group, a chloroethylene group, a bromoethylene group, a methyltrimethylene group, a dimethyltrimethylene group, a methoxytrimethylene group, an ethoxytrimethylene group, a chlorotrimethylene group, and a bromotrimethylene group. Among them, a linear alkylene group such as a methylene group, an ethylene group, a trimethylene group or a tetramethylene group is preferred, and an ethylene group is particularly preferred.

E in the formula (I) is a residue of folic acid or a folic acid derivative, which means folic acid or a folic acid derivative as represented by $E-CO_2H$. The moiety E is not particularly limited as long as it is folic acid or a folic acid derivative having a carboxy group, and examples thereof in the form of $E-CO_2H$ include folic acid, methotrexate, aminopterin, pralatrexate, plevitrexed, edatrexate, pemetrexed, raltitrexed, and lometrexol. Among them, methotrexate, pemetrexed and the like are preferred.

The polymer conjugate of the present invention may be, for example, a compound represented by the formula (II).

Examples of the (C1-C6) alkyl group which may be substituted for D in the formula (II) include a methyl group, an ethyl group, an n-propyl group, an i-propyl group, an n-butyl group, an s-butyl group, a t-butyl group, an n-pentyl group, an n-hexane group, a benzyl group, a dimethoxyethyl group, a diethoxyethyl group, an aminomethyl group, an aminoethyl group, a 3-aminopropyl group and a 4-aminobutyl group. The moiety D is preferably an unsubstituted (C1-C6) alkyl group, and among others, a methyl group is particularly preferred.

In the formula (II), the average value of n is about 5 to 11500, preferably about 50 to 1000, and more preferably about 100 to 300.

Examples of the (C2-C6) alkylene group for J in the formula (II) include linear alkylene groups such as an ethylene group, a trimethylene group, a tetramethylene group and a hexamethylene group, and among them, a trimethylene group is preferred.

In the formula (II), c+d+e represents the total number of aspartic acid residues in one molecule of the polymer conjugate, and the average value is about 3 to 200, preferably about 5 to 100, and more preferably about 6 to 60. The various constituent units of the polyaspartic acid may be randomly linked or may be linked in the form of blocks. c+d is an integer, and e may be zero.

Furthermore, the proportion of the α-amino acid type constituent unit (c) with respect to the total number of aspartic acid residues is preferably 10 to 100%, and particularly preferably 20 to 100%. This proportion can be appropriately changed by, for example, selecting the deprotection conditions for the protective group of polyaspartic acid or the like in the processes of the production method according to Patent Document 1 or the like.

Examples of the (C1-C6) acyl group for B in the formula (II) include a formyl group, an acetyl group, a propionyl group, a butyryl group, a valeryl group, an isovaleryl group, a pivaloyl group, and a hexanoyl group. B is preferably a (C2-C4) acyl group, for example, an acetyl group or a propionyl group, and an acetyl group is particularly preferred.

R in the formula (II) may be a hydroxy group or a substituent represented by the formula (I), and at least one of R in one molecule is the substituent represented by the formula (I). The substituent represented by the formula (I) is as described above, and is preferably the substituent represented by the formula (III). E in the formula (III) has the same definition as E in the formula (I), and has the same preferable definitions as well.

Next, in regard to the polymer conjugate of folic acid or a folic acid derivative of the present invention, the case in which the folic acid derivative is methotrexate and the linker molecule is tyramine (4-aminoethylphenol) will be explained, but the present invention is not intended to be limited to this compound.

Since methotrexate has two carboxy groups, the compound having tyramine and methotrexate linked via an ester bond also has two regioisomers. As shown below, an isomer in which the α-carboxy group of glutamic acid which is a partial structure of methotrexate is linked to tyramine, is referred to as an α-substituted form, and an isomer in which the γ-carboxy group is linked to tyramine is referred to as a γ-substituted form.

The reaction temperature of the dehydration-condensation reaction is usually 4 to 60° C., and preferably 15 to 50° C., and the reaction time is one hour to several days, and preferably 4 to 48 hours.

The organic solvent is not particularly limited as long as the reaction proceeds, but examples include aromatic hydrocarbons such as toluene and xylene; halogenated hydrocarbons such as methylene chloride, chloroform and 1,2-dichloroethane; ethers such as tetrahydrofuran, dioxane, dimethoxyethane, and diethylene glycol dimethyl ether; nitriles such as acetonitrile and propionitrile; amides such as dimethylforamide, dimethylacetamide and N-methylpyrrolidone; ureas such as 1,3-dimethylimidazolidinone; and mixed solvents of the solvents mentioned above. Preferred examples include amides and ureas, and more preferred examples include dimethylformamide and 1,3-dimethylimidazolidinone.

[Chemical Formula 6]

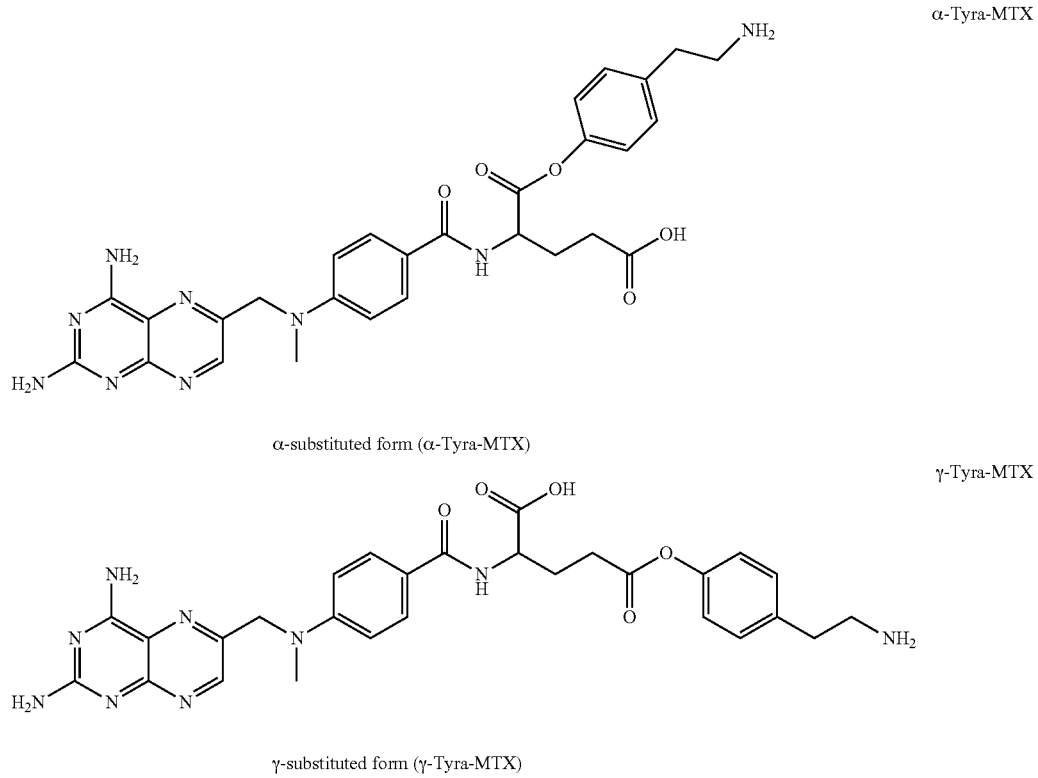

α-substituted form (α-Tyra-MTX)

γ-substituted form (γ-Tyra-MTX)

The method for producing these compounds will be described.

First, the amino group of tyramine is protected with a protective group that is removable after preparation of an ester bond. The protective group is not particularly limited as long as it is a general protective group for an amino group. However, preferred is a protective group that can be removed under the deprotection conditions in which the ester bond of tyramine and methotrexate is stable, that is, under neutral or acidic conditions, and examples include a benzyloxycarbonyl group, a t-butoxycarbonyl (Boc) group, and an allyloxycarbonyl group.

Subsequently, tyramine with the amino group protected is condensed by dehydration with methotrexate in an organic solvent using a dehydration-condensation agent.

The dehydration-condensation agent is not particularly limited as long as the condensation reaction of the amine and the carboxy group proceeds, but preferred examples include dicyclohexylcarbodiimide, diisopropylcarbodiimide, 1-dimethylaminopropyl-3-ethylcarbodiimide, carbonyldiimidazole, isobutyl chloroformate, pivalic acid chloride, DMT-MM (4-(4,6-dimethoxy-1,3,5-triazin-2-yl)-4-methylmorpholinium chloride), TFFH (tetramethylfluoroformamidinium hexafluorophosphate), 1-ethoxycarbonyl-2-ethoxy-1,2-dihydroxyquinolinone (EEDQ), and BOP (benzotriazol-1-yloxytris(dimethylamino)phosphonium hexafluorophosphate).

During the dehydration-condensation reaction, a reaction aid may be used. Examples of the reaction aid include N-hydroxysuccinimide, 1-hydroxybenzotriazole, 4-dimethylaminopyridine, and 2,6-di-t-butyl-4-methylpyridine.

After the dehydration-condensation reaction, appropriate purification treatments are carried out as necessary, and thus the α-substituted form and the γ-substituted form, each with the amino group of tyramine being protected, are obtained as a mixture or separately. Furthermore, the protective group of the amino group is subjected to an appropriate treatment to deprotect it, and thus the condensed compound of methotrexate and tyramine (α-substituted form, γ-substituted form or a mixture thereof) is obtained.

The present invention also includes a method for producing a polymer conjugate of folic acid or a folic acid derivative, the method including linking the folic acid or a folic acid derivative to the phenolic hydroxy group of a compound represented by formula (IV) via an ester bond, removing the protective group of the amino group, and subsequently linking the resulting deprotection product to a block copolymer composed of a polyethylene glycol and a polymer having a carboxy group in a side chain, through dehydration-condensation with the carboxy group, to produce an amide bond.

Subsequently, the production method will be explained.

The substituted isomer obtained as described above is dehydration-condensed with a methoxypolyethylene glycol-polyaspartic acid block copolymer or a methoxypolyethylene glycol-polyglutamic acid block copolymer produced according to the method described in Patent Document 3 or the like, in an organic solvent, using a dehydration-condensation agent.

The reaction temperature of the dehydration-condensation reaction is usually 4 to 60° C., and preferably 15 to 50° C., and the reaction time is one hour to several days, and preferably 4 to 48 hours.

Examples of the organic solvent include the same organic solvents as the organic solvents used in the condensation reaction of methotrexate and tyramine with a protected amino group, and the same applies to the preferred examples of the organic solvent.

Examples of the dehydration-condensation agent include the same dehydration-condensation agents as the dehydration-condensation agents used in the condensation reaction of methotrexate and tyramine with a protected amino group.

During the dehydration-condensation reaction, a reaction aid may be used, and examples of the reaction aid include the same reaction aids as the reaction aids used in the condensation reaction of methotrexate and tyramine with a protected amino group.

However, since the substituted isomer obtained as described above have free carboxy groups remaining therein, it is preferable to initially activate the side chain carboxy group of the block copolymer, and then allowing the carboxy group with the amino group of the substituted isomer.

As the method of activation, a method that is usually used upon the production of peptide bonds can be applied, and for example, a method of using the reagents used above may be mentioned, that is, a method of condensing a carboxylic acid and a reaction aid such as N-hydroxysuccinimide using the dehydration-condensation agent mentioned above, isolating the product as an active ester form, and adding an amine to obtain an amide.

For the polymer conjugate of folic acid or a folic acid derivative of the present invention, the amount of the folic acid or the folic acid linked to the block copolymer composed of a polyethylene glycol and a polymer having a carboxy group in a side chain via a linker, is not particularly limited as long as it is an amount that exhibits efficacy, but the amount is usually 1 to 100%, and preferably 10 to 90%, of the total number of carboxy groups in the polymer.

The amount of linked folic acid and folic acid derivative can be determined from, for example, the intensity of the ultraviolet absorption spectrum. The amount can also be determined by quantifying folic acid or the folic acid derivative that has been released by alkali hydrolyzing the polymer conjugate of folic acid or the folic acid derivative of the present invention, for example, by using high performance liquid chromatography (HPLC).

In the polymer conjugate of folic acid or a folic acid derivative of the present invention, the carboxy group in the side chain that is not linked to the linker molecule or the carboxy group of the folic acid and the folic acid derivative that is not ester may be in a free form or in a salt form. When the carboxy group is obtainable in a free form, the carboxy group can be converted to a desired salt according to a method known per se or a method equivalent thereto. When the carboxy group is obtainable as a salt, the carboxy group can be converted to a free form or another desired salt by a method known per se or a method equivalent thereto.

Examples of the salt include a lithium salt, a sodium salt, a potassium salt, a magnesium salt, an ammonium salt and a triethylammonium salt.

The polymer conjugate of folic acid or a folic acid derivative of the present invention may form, in water, micelles having the polyethylene glycol as the outer shell. When the polymer conjugate forms micelles, satisfactory water-solubility, stability in an aqueous solution, and enhancement of the efficacy are expected.

The present invention also encompasses an anticancer drug, a therapeutic agent for inflammatory diseases and an anti-rheumatoid agent, each containing the polymer conjugate of folic acid or a folic acid derivative described above, as an active ingredient. This polymer conjugate of folic acid or a folic acid derivative can be directly administered, or can be administered as a pharmaceutical composition mixed with pharmaceutically acceptable materials. The dosage form of the pharmaceutical composition may be any of an injectable preparation, a powder, a granule, a tablet, a suppository and the like. Furthermore, these preparations may also contain various auxiliary agents used for medical purposes, that is, a carrier and other auxiliary agents, for example, additives such as a stabilizer, a preservative, a pain soothing agent and an emulsifier.

The content of the polymer conjugate of folic acid and the folic acid derivative in the preparation may vary in a wide range with different preparations, but the content is usually 0.1 to 100% by weight, and preferably 1 to 98% by weight.

EXAMPLES

Hereinafter, the present invention will be described in more detail by way of Reference Examples, Examples and Test Examples, but the present invention is not intended to be limited to these.

Reference Example 1

Synthesis of Boc-Tyramine

Tyramine (5.49 g) was dissolved in 110 mL of dioxane and 110 mL of water, and $(Boc)_2O$ (di-t-butyl dicarbonate: 9.60 g) was added thereto. The mixture was stirred for 4 hours at room temperature and then was extracted with ethyl acetate. The organic layer was dehydrated with anhydrous sodium sulfate, and then the dehydrated organic layer was concentrated under reduced pressure. The residue was purified by silica gel column chromatography (hexane-ethyl acetate), and the target fraction was concentrated under reduced pressure. Thus, Boc-Tyramine (9.05 g) was obtained.

Reference Example 2

Synthesis of Boc-Tyramine-MTX

MTX (methotrexate: 8.18 g), Boc-Tyramine (8.54 g) and DMAP (dimethylaminopyridine: 4.40 g) were dissolved in DMF (dimethylformamide: 164 mL), and then diisopropylcarbodiimide (5.64 mL) was added thereto. The mixture was stirred for 4 hours at room temperature and then was extracted with ethyl acetate (1.64 L) and water (1.64 L). 2.9 L of a 20 mM citrate buffer solution (pH 4.6) was added to the aqueous layer, and a precipitate thus produced was filtered using a Kiriyama funnel. The precipitate thus obtained was dissolved in a mixed solvent of methylene chloride-ethanol (1:1) and dehydrated with anhydrous sodium sulfate, and then the solvent was distilled off under reduced pressure. The residue was purified by silica gel column chromatography, and thus two kinds of MTX monoester forms (α-monoester form: 1.711 g, γ-monoester form: 1.332 g) were obtained. The α-monoester form and the γ-monoester form had retention times of 13.3 minutes and 13.7 minutes, respectively, under the HPLC condition 1.

HPLC Condition 1
Column: Inertsil ODS-3 (5 μm) 4.6×150 mm
Column temperature: 40° C.
Eluent: Liquid A: 0.1% aqueous solution of phosphoric acid, Liquid B: acetonitrile
Gradient

| Time (min): | 0 | 30 | 35 | 35.1 | 45 |
|---|---|---|---|---|---|
| Liquid B (%): | 10 | 90 | 90 | 10 | 10 |
| Flow rate: | 1.0 mL/min | | | | |
| Detector: | UV (254 nm) | | | | |

Reference Example 3

Synthesis of Boc-Tyramine-PEM

Pemetrexed (PEM: 624 mg) obtained by the method described in J. Med. Chem., 35, p. 4450-4454 (1992), Boc-Tyramine (693 mg), and DMAP (357 mg) were dissolved in DMF (12.5 mL), and then diisopropylcarbodiimide (457 μL) was added thereto. The mixture was stirred for 45 minutes at room temperature, and then acetic acid (334 μL) was added thereto. Purification was carried out under HPLC Condition 2, and thus 277 mg of Boc-Tyramine-PEM (mixture of α,γ-monoesters:about 1:1) was obtained. The α-ester and the γ-ester had retention times of 18.0 minutes and 18.3 minutes, respectively, under the HPLC Condition 1.

HPLC Condition 2
Column: Inertsil ODS-3 (5 μm) 20×250 mm
Column temperature: Room temperature
Eluent: Liquid A: 0.1% aqueous solution of trifluoroacetic acid, Liquid B: acetonitrile
Gradient

| Time (min): | 0 | 4.9 | 5 | 13 | 13.1 | 20 | 20.1 | 30 |
|---|---|---|---|---|---|---|---|---|
| Liquid B (%): | 10 | 10 | 20 | 20 | 40 | 40 | 10 | 10 |
| Flow rate: | 20 mL/min | | | | | | | |
| Detector: | UV (254 nm) | | | | | | | |

Reference Example 4

Synthesis of α-Tyramine-MTX

Ethyl acetate (1.5 mL) was added to α-Boc-Tyramine-MTX (100 mg) obtained in Reference Example 2 to suspend the compound, and then 4 N HCl/EtOAc (0.5 mL) was added thereto. The mixture was stirred for one hour at room temperature. A precipitate thus obtained was filtered with a Kiriyama funnel and dried in a vacuum, and thus α-Tyramine-MTX (111 mg) was obtained. The compound is thought to be a trihydrochloride salt, based on yield.

Reference Example 5

Synthesis of γ-Tyramine-MTX

Ethyl acetate (1.5 mL) was added to γ-Boc-Tyramine-MTX (100 mg) obtained in Reference Example 2 to suspend the compound, and then 4 N HCl/EtOAc (0.5 mL) was added thereto. The mixture was stirred for one hour at room temperature. A precipitate thus obtained was filtered with a Kiriyama funnel and dried in a vacuum, and thus γ-Tyramine-MTX (108 mg) was obtained. The compound is thought to be a trihydrochloride salt, based on yield.

Reference Example 6

Synthesis of Tyramine-PEM (α,γ-mixture)

Ethyl acetate (1.5 mL) was added to 100 mg of Boc-Tyramine-PEM (α,γ-mixture) obtained in Reference Example 3 to suspend the compound, and then 4 N HCl/dioxane (0.5 mL) was added thereto. The mixture was stirred for one hour at room temperature. A precipitate thus obtained was filtered with a Kiriyama funnel and dried in a vacuum, and thus 93 mg of Tyramine-PEM (α,γ-mixture) was obtained. The compound is thought to be a dihydrochloride salt, based on yield.

Reference Example 7

Synthesis of PEG-Asp33(OSu)-Ac

PEG-Asp33-Ac (N-acetyl compound of block copolymer of one-terminal methyl, the other-terminal aminopropyl polyethylene glycol and polyaspartic acid (33 units): 485 mg), and HOSu (N-hydroxysuccinimide: 115 mg) were dissolved in DMF (9.7 mL), and the mixture was warmed in an oil bath at 33° C. DCC (dicyclohexylcarbodiimide: 206 mg) was added thereto, and the mixture was stirred for one hour. The urea thus produced was filtered with a Kiriyama funnel, and ethyl acetate (39 mL) was added to the obtained filtrate to dilute the filtrate. Then, hexane (58 mL) was added thereto, and crystals were precipitated. After the mixture was stirred for 15 minutes, stirring was stopped, and the supernatant was removed. A mixed solvent of hexane-ethyl acetate (3:2) was further added to the residue, and the mixture was stirred. A precipitate thus produced was filtered with a Kiriyama funnel and dried in a vacuum, and thus PEG-Asp33(OSu)-Ac (454 mg) was obtained.

Example 1

Synthesis of PEG-Asp33(α-Tyramine-MTX)-Ac

PEG-Asp33(OSu)-Ac (150 mg) obtained in Reference Example 7 and α-Tyramine-MTX (113 mg) obtained in Reference Example 4 were dissolved in DMF (1.5 mL), and triethylamine (69 μL) was added thereto. The mixture was stirred for 4 hours at room temperature, and then the mixture was added dropwise to 100 mL of a mixed solvent of hexane-ethyl acetate (4:1). After the mixture was stirred for 10 minutes, stirring was stopped, and the supernatant was removed. Furthermore, a mixed solvent of hexane-ethyl acetate (4:1) was added to the residue, and the mixture was stirred. A precipitate thus obtained was filtered with a Kiriyama funnel and dried in a vacuum, and thus crude crystals of the target compound (261 mg) were obtained.

These crude crystals were dissolved in 52 mL of a mixed solvent of acetonitrile-water (1:1), and ion-exchange resins, Muromac (registered trademark) C1002 (2.61 g) and Muromac (registered trademark) $A_2O_3T$ (2.61 g) (both manufactured by Muromachi Technos Co., Ltd.), were added to the solution to purify the solution by adsorbing impurities. The resins were filtered, and then the filtrate was concentrated under reduced pressure and freeze-dried, and thus PEG-Asp33(α-Tyramine-MTX)-Ac (172 mg) was obtained. The MTX content of this polymer conjugate was 19.6% (w/w). The drug (MTX) content was calculated by hydrolyzing the obtained polymer conjugate with an aqueous solution of sodium hydroxide, and analyzing the drug (MTX) in a free form by HPLC. The same applies to the polymer conjugates that will be described below.

Example 2

Synthesis of PEG-Asp33(γ-Tyramine-MTX)-Ac

PEG-Asp33(OSu)-Ac (146 mg) obtained in Reference Example 7 and γ-Tyramine-MTX (110 mg) obtained in Reference Example 5 were dissolved in DMF (1.5 mL), and triethylamine (67 μL) was added thereto. The mixture was stirred for 4 hours at room temperature, and then the mixture was added dropwise to 100 mL of a mixed solvent of hexane-ethyl acetate (4:1). After the mixture was stirred for 10 minutes, stirring was stopped, and the supernatant was removed. Furthermore, a mixed solvent of hexane-ethyl acetate (4:1) was added to the residue, and the mixture was stirred. A precipitate thus obtained was filtered with a Kiriyama funnel and dried in a vacuum, and thus crude crystals of the target compound (270 mg) were obtained.

These crude crystals were dissolved in 54 mL of a mixed solvent of acetonitrile-water (1:1), and ion-exchange resins, Muromac (registered trademark) C1002 (2.70 g) and Muromac (registered trademark) $A_2O_3T$ (2.70 g), were added to the solution to purify the solution by adsorbing impurities. The resins were filtered, and then the filtrate was concentrated under reduced pressure and freeze-dried, and thus PEG-Asp33(γ-Tyramine-MTX)-Ac (170 mg) was obtained. The MTX content of this polymer conjugate was 25.0% (w/w).

Reference Example 8

Synthesis of PEG-Asp40(OSu)-Ac

PEG-Asp40-Ac (N-acetyl compound of block copolymer of one-terminal methyl, the other-terminal aminopropyl polyethylene glycol and polyaspartic acid (40 units): 420 mg), and HOSu (115 mg) were dissolved in DMF (8.4 mL), and the mixture was warmed in an oil bath at 37° C. DCC (206 mg) was added thereto, and the mixture was stirred for one hour. The urea thus produced was filtered with a Kiriyama funnel, and ethyl acetate (34 mL) was added to the obtained filtrate to dilute the filtrate. Then, hexane (50 mL) was added thereto, and crystals were precipitated. After the mixture was stirred for 40 minutes, stirring was stopped, and the supernatant was removed. A mixed solvent of hexane-ethyl acetate (4:1) was further added to the residue, and the mixture was stirred. A precipitate thus produced was filtered with a Kiriyama funnel and dried in a vacuum, and thus PEG-Asp40(OSu)-Ac (424 mg) was obtained.

Example 3

Synthesis of PEG-Asp40(α-Tyramine-MTX)-Ac

PEG-Asp40(OSu)-Ac (220 mg) obtained in Reference Example 8 and α-Tyramine-MTX (177 mg) obtained in Reference Example 4 were dissolved in DMF (2.2 mL), and triethylamine (109 μL) was added thereto. The mixture was stirred for 4 hours at room temperature, and then the mixture was added dropwise to 100 mL of a mixed solvent of hexane-ethyl acetate (4:1). After the mixture was stirred for 70 minutes, stirring was stopped, and the supernatant was removed. Furthermore, a mixed solvent of hexane-ethyl acetate (4:1) was added to the residue, and the mixture was stirred. A precipitate thus obtained was filtered with a Kiriyama funnel and dried in a vacuum, and thus crude crystals of the target compound (413 mg) were obtained.

These crude crystals were dissolved in 83 mL of a mixed solvent of acetonitrile-water (1:1), and ion-exchange resins, Muromac (registered trademark) C1002 (4.13 g) and Muromac (registered trademark) $A_2O_3T$ (4.13 g), were added to the solution to purify the solution by adsorbing impurities. The resins were filtered, and then the filtrate was concentrated under reduced pressure and freeze-dried, and thus PEG-Asp40(α-Tyramine-MTX)-Ac (263 mg) was obtained. The MTX content of this polymer conjugate was 23.6% (w/w).

Example 4

Synthesis of PEG-Asp40(γ-Tyramine-MTX)-Ac

PEG-Asp40(OSu)-Ac (100 mg) obtained in Reference Example 8 and γ-Tyramine-MTX (81 mg) obtained in Reference Example 5 were dissolved in DMF (1.0 mL), and triethylamine (49 μL) was added thereto. The mixture was stirred for 4 hours at room temperature, and then the mixture was added dropwise to 100 mL of a mixed solvent of hexane-ethyl acetate (4:1). After the mixture was stirred for 25 minutes, stirring was stopped, and the supernatant was removed. Furthermore, a mixed solvent of hexane-ethyl acetate (4:1) was added to the residue, and the mixture was stirred. A precipitate thus obtained was filtered with a Kiriyama funnel and dried in a vacuum, and thus crude crystals of the target compound (189 mg) were obtained.

These crude crystals were dissolved in 38 mL of a mixed solvent of acetonitrile-water (1:1), and ion-exchange resins, Muromac (registered trademark) C1002 (1.89 g) and Muromac (registered trademark) $A_2O_3T$ (1.89 g), were added to the solution to purify the solution by adsorbing impurities. The resins were filtered, and then the filtrate was concentrated under reduced pressure and freeze-dried, and thus PEG-Asp40(γ-Tyramine-MTX)-Ac (126 mg) was obtained. The MTX content of this polymer conjugate was 28.6% (w/w).

Example 5

Synthesis of PEG-Asp40(α,γ-Tyramine-PEM)-Ac

PEG-Asp40(OSu)-Ac (129 mg) obtained in Reference Example 8 and Tyramine-PEM (α,γ-mixture: 93 mg) obtained in Reference Example 6 were dissolved in DMF (1.3 mL), and triethylamine (42 μL) was added thereto. The mixture was stirred for 2.5 hours at room temperature, and then the mixture was added dropwise to 130 mL of a mixed solvent of hexane-ethyl acetate (4:1). After the mixture was stirred for 10 minutes, stirring was stopped, and the supernatant was removed. Furthermore, a mixed solvent of hexane-ethyl acetate (4:1) was added to the residue, and the mixture was stirred. A precipitate thus obtained was filtered with a Kiriyama funnel and dried in a vacuum, and thus crude crystals of the target compound (246 mg) were obtained.

These crude crystals were dissolved in 50 mL of a mixed solvent of acetonitrile-water (1:1), and ion-exchange resins, Muromac (registered trademark) C1002 (2.5 g) and Muromac (registered trademark) $A_2O_3T$ (2.5 g), were added to the solution to purify the solution by adsorbing impurities. The resins were filtered, and then the filtrate was concentrated under reduced pressure and freeze-dried, and thus PEG-Asp40(α,γ-Tyramine-PEM)-Ac (150 mg) was obtained. The PEM content of this polymer conjugate was 22.1% (w/w).

Reference Example 9

Synthesis of PEG-Asp44(OSu)-Ac

PEG-Asp44-Ac (N-acetyl compound of block copolymer of one-terminal methyl, the other-terminal aminopropyl polyethylene glycol and polyaspartic acid (44 units): 582 mg), and HOSu (173 mg) were dissolved in DMF (11.6 mL), and the mixture was warmed in an oil bath at 37° C. DCC (309 mg) was added thereto, and the mixture was stirred for one hour. The urea thus produced was filtered with a Kiriyama funnel, and ethyl acetate (46 mL) was added to the obtained filtrate to dilute the filtrate. Then, hexane (70 mL) was added thereto, and crystals were precipitated. After the mixture was stirred for 30 minutes, stirring was stopped, and the supernatant was removed. A mixed solvent of hexane-ethyl acetate (4:1) was further added to the residue, and the mixture was stirred. A precipitate thus produced was filtered with a Kiriyama funnel and dried in a vacuum, and thus PEG-Asp44(OSu)-Ac (543 mg) was obtained.

Example 6

Synthesis of PEG-Asp44(γ-Tyramine-MTX)-Ac

PEG-Asp44(OSu)-Ac (100 mg) obtained in Reference Example 9 and γ-Tyramine-MTX (57 mg) obtained in Reference Example 5 were dissolved in DMF (2 mL), and triethylamine (35 µL) was added thereto. The mixture was stirred for 4 hours at room temperature, and then the mixture was added dropwise to 100 mL of a mixed solvent of hexane-ethyl acetate (4:1). After the mixture was stirred for 15 minutes, stirring was stopped, and the supernatant was removed. Furthermore, a mixed solvent of hexane-ethyl acetate (4:1) was added to the residue, and the mixture was stirred. A precipitate thus obtained was filtered with a Kiriyama funnel and dried in a vacuum, and thus crude crystals of the target compound (158 mg) were obtained.

These crude crystals were dissolved in 32 mL of a mixed solvent of acetonitrile-water (1:1), and ion-exchange resins, Muromac (registered trademark) C1002 (1.58 g) and Muromac (registered trademark) $A_2O_3T$ (1.58 g), were added to the solution to purify the solution by adsorbing impurities. The resins were filtered, and then the filtrate was concentrated under reduced pressure and freeze-dried, and thus PEG-Asp44(γ-Tyramine-MTX)-Ac (109 mg) was obtained. The MTX content of this polymer conjugate was 22.7% (w/w).

Test Example 1

Measurement of Drug Release Rate (Drug Release in the Absence of Hydrolase

Approximately 5 mg of a sample was weighed and dissolved in acetonitrile (250 µL) and water (250 µL) (solution A). A 0.1 N sodium hydroxide solution (900 µL) was added to the solution A (100 µL), and the mixture was left to stand at room temperature for one hour. 50 µL of this solution was sampled and neutralized with 50 µL of 0.1 N hydrochloric acid, and then the neutralized solution was diluted with a PBS solution (400 µL). This solution was analyzed by HPLC, and the result was taken as the reference value of the total amount of drug contained in the sample.

On the other hand, the solution A (200 µL) was diluted with the PBS solution (1800 µL), and then the dilution was left to stand in a constant temperature bath at 37° C. Sampling was carried out over time, and the sampled aliquots were analyzed by HPLC. The peak area of the drug was compared with the reference peak of the total amount of drug, and the drug release ratios at various time points were calculated. The obtained results are presented in Table 1.

In FIG. 1, MTX_A-33 represents PEG-Asp33(α-Tyramine-MTX)-Ac obtained in Example 1; MTX_G-33 represents PEG-Asp33(γ-Tyramine-MTX)-Ac obtained in Example 2; MTX-G-44 represents PEG-Asp44(γ-Tyramine-MTX)-Ac obtained in Example 6; MTX_G-40 represents PEG-Asp40(γ-Tyramine-MTX)-Ac obtained in Example 4; MTX_A-40 represents PEG-Asp40(α-Tyramine-MTX)-Ac obtained in Example 3; and PEM_G-40 represents PEG_Asp40(α,γ-Tyramine-PEM)-Ac obtained in Example 5.

As is obvious from FIG. 1, the polymer conjugate of folic acid or a folic acid derivative of the present invention can release a drug in the absence of an enzyme, and the drug release rate depends on the degree of acidity of the carboxylic acid in the drug molecule such that the release rate of the α-substituted form is faster than the release rate of the γ-substituted form. In the case of PEM_G-40, since a mixture of α-form and γ-form is bound to the polymer conjugate, the release rate is intermediate between the rate of the α-substituted form and the rate of the γ-substituted form. This shows that the drug release rate can be controlled by mixing the α-substituted form and the γ-substituted for at an appropriate ratio.

Test Example 2

Antitumor Effect on Mouse Colon Cancer Colon 26-transplanted Mouse

Mouse colon cancer Colon 26 cells subcutaneously subcultured in a BALB/c mouse were prepared in the form of a block which measured about 2 mm on each side, and the block was subcutaneously transplanted on the dorsal part of a CDF1 mouse using a trocar. On the 7th day after the tumor transplantation, the polymer conjugates of the present invention, MTX_A-40 (PEG-Asp40(α-Tyramine-MTX)-Ac obtained in Example 3 and MTX_G-44 (PEG-Asp44(γ-Tyramine-MTX)-Ac obtained in Example 6, and MTX as a comparative substance were administered through the tail vein. The polymer conjugates of the present invention were respectively dissolved in water for injection and were administered once. MTX as a control was dissolved and diluted in distilled water and was administered once a day for 5 successive days. After the administration, the major axis (L mm) and minor axis (W mm) of the tumor was regularly measured, and the tumor volume was calculated by the formula: $(L \times W^2)/2$. The tumor volume on the day of initiation of administration was taken as 1.0, and while taking the 12th day after the initiation of administration as the day of determination, the relative tumor volume of each administered group was determined. The results are presented in Table 1. The dose in the compounds of the present invention is converted to that of MTX.

TABLE 1

Antitumor effect on mouse colon cancer Colon 26 transplantation

| Compound | Administration schedule | Single dose mg/kg/day | Total amount administered mg/kg | Relative tumor volume * mean ± SD | Toxicity (death/n) |
|---|---|---|---|---|---|
| Untreated group | — | — | — | 12.3 ± 4.9 | 0/5 |
| MTX | Sequential Administered for 5 days | 20 | 100 | — | 3/3 |
| | | 15 | 75 | 12.2 ± 8.1 | 0/3 |
| MTX_A-40 | Once | 50 | 50 | 4.8 ± 2.8 | 1/3 |
| | | 25 | 25 | 6.8 ± 0.7 | 0/3 |
| MTX_G-44 | Once | 50 | 50 | 0.4 ± 0.1 | 1/3 |
| | | 25 | 25 | 2.3 ± 1.1 | 1/3 |
| | | 12.5 | 12.5 | 8.2 ± 1.0 | 0/3 |

* Mean relative tumor volume on the 12th day after the initiation of administration when the tumor volume on the day of initiation of administration was taken as 1.0

The relative tumor volume of the untreated group on the day of determination was 12.3.

When MTX was administered at a dose of 20 mg/kg for 5 successive days, all of the animals died of toxicity. The relative tumor volume for the dose of 15 mg/kg was 12.2, which was not much different from the relative tumor volume of the untreated group, and an antitumor effect was not observed.

On the other hand, when the polymer conjugate MTX_A-40 of the present invention was administered at a dose of 50 mg/kg in terms of MTX, one animal died of toxicity, but the relative tumor volume was 4.8. At a dose of 25 mg/kg of the same polymer conjugate, the relative tumor volume was 6.8, and tumor growth is suppressed in a manner dependent on the amount of administration. When MTX_G-44 was administered at a dose of 25 mg/kg in terms of MTX, one animal died of toxicity, but the relative tumor volume was 2.3. At a dose of 12.5 mg/kg of the same polymer conjugate, the relative tumor volume was 8.2, and the tumor growth is suppressed in a manner dependent on the amount of administration.

As discussed above, the polymer conjugates of MTX of the present invention (MTX_A-40 and MTX_G-44) strongly suppress the growth of tumor with a single administration, and the effects highly surpass the effects of successively administered MTX. Thus, the polymer conjugates are useful as anticancer drugs.

Test Example 3

Anti-Inflammatory Evaluation Using Rat Collagen-induced Arthritis Model

An emulsion of bovine type II collagen II and Freund's incomplete adjuvant was subcutaneously administered (sensitized) to the dorsal part of a DA/Slc rat at 4 dorsal intradermal sites in a total amount of 0.4 mL, and thereby arthritis was induced. MTX_A-40 (PEG-Asp40(α-Tyramine-MTX)-Ac) obtained in Example 3 and MTX as a comparative substance were respectively prepared into a 5 mg/mL aqueous solution, and the solutions were used in the administration. Leflunomide as a positive control substance was suspended in an aqueous solution of carboxymethylcellulose sodium salt (CMC), and the suspension was used in the administration. The group administered with 2.5 mg/kg of MTX_A-40 (in terms of MTX; high-dosage group) was administered with the drug through the tail vein on the 1st day after sensitization, and the group administered with 1.25 mg/kg of MTX_A-40 (in terms of MTX; low-dosage group) and the group administered with 2.5 mg/kg of MTX were administered with the drug on the 1st day and 8th day after sensitization. Leflunomide (10 mg/kg) was forcedly orally administered for 28 successive days from the day of sensitization. After the sensitization, the left footpad of the rat was monitored, and the developed arthritis was scored. The results are presented in FIG. 2. The score criteria for arthritis given in Table 2 were used for the scoring.

TABLE 2

| Score | State of arthritis |
|---|---|
| 0 | Normal |
| 1 | Rashes are observed. |
| 2 | Rashes and light edema in the toes are observed. |
| 3 | Edema has spread from the toes to the entire foot. |
| 4 | Severe edema is observed. |
| 5 | Arthritic deformation is observed. |

Figure 2:
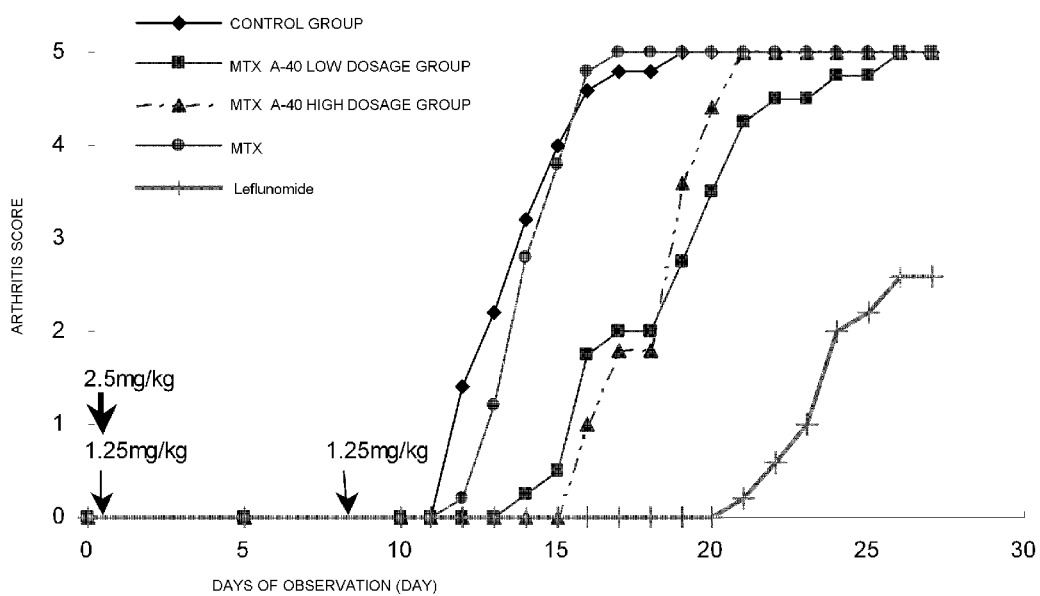
FIG. 2 is a diagram showing the anti-inflammatory evaluation results in Test Example 2 obtained by using the rat collagen-induced arthritis model.

As it is obvious from FIG. 2, the MTX-administered group developed inflammation almost simultaneously with the control group, and no anti-inflammatory effects were observed.

On the other hand, the MTX_A-40-administered group delayed the time of onset of inflammation, despite that the total amount of administration was only a half of the total amount of MTX. Thus, it was confirmed that the polymer conjugate of MTX enhances and sustains the anti-inflammatory action of MTX. This shows that the polymer conjugate of folic acid or a folic acid derivative of the present invention are useful as a therapeutic drug for inflammatory diseases.

Test Example 4

Anti-inflammatory Evaluation 2 Using Rat Collagen-induced Arthritis Model

MTX_G-40 (PEG-Asp40(γ-Tyramine-MTX)-Ac) obtained in Example 4 and MTX as a comparative substance were respectively prepared into a 5 mg/mL aqueous solution, and the aqueous solutions were used in the administration. The test was carried out in the same manner as in Test Example 3. Leflunomide as a positive control substance was suspended in an aqueous solution of carboxymethylcellulose sodium salt (CMC), and the suspension was used in the administration. The groups administered with 1.00 mg/kg (convert to dose of MTX) and 1.25 mg/kg (convert to dose of MTX) of MTX_G-40, and the group administered with 2.5 mg/kg of MTX were administered with the drug through the tail vein on the 1st day, 8th day, 15th day and 22nd day after sensitization. Leflunomide (10 mg/kg) was forcedly orally administered for 28 successive days from the day of sensitization. After the sensitization, the left footpad of the rat was monitored, and the developed arthritis was scored using the criteria shown in the above Table 2. The results are presented in FIG. 3.

Figure 3:
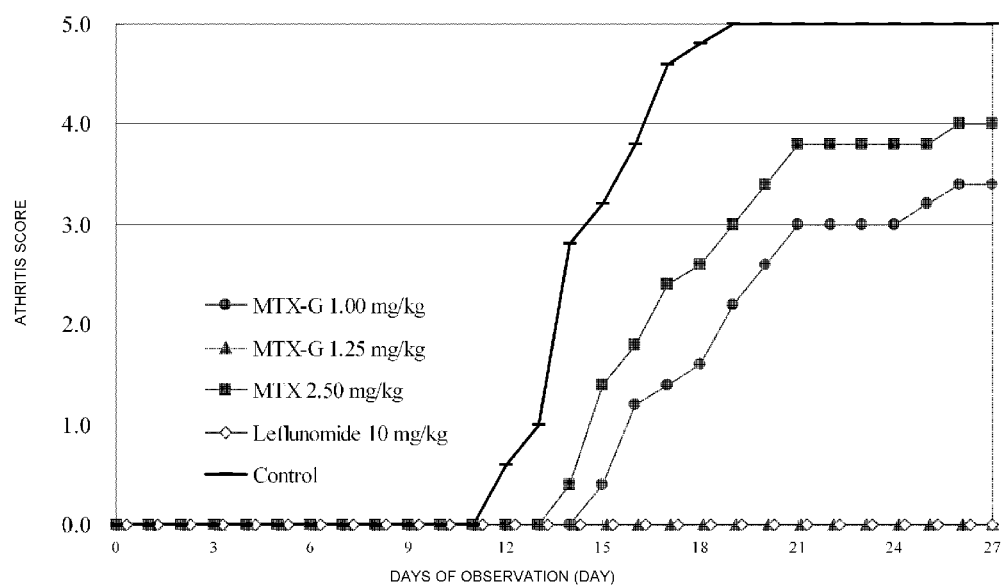
FIG. 3 is a diagram showing the anti-inflammatory evaluation results in Test Example 3 obtained by using the rat collagen-induced arthritis model.

As it is obvious from FIG. 3, in the current test, the MTX-administered group delayed the time of onset of inflammation as compared with the control group. On the other hand, MTX_G-40 further delayed the time of onset of inflammation compared to MTX, only with an administration of 1.00 mg/kg, which is a low dosage. The group administered with 1.25 mg/kg of MTX_G-40 completely suppressed the onset of inflammation for the 28 days of monitoring. Thus, it was confirmed that the polymer conjugate of MTX enhances and sustains the anti-inflammatory effect of MTX.

The invention claimed is:

1. A polymer conjugate of methotrexate or pemetrexed or a pharmacologically acceptable salt thereof, in which the nitrogen atom bound to the group represented by G of a substituent represented by the following formula (I) is amid-linked to a carboxy group of a side chain of a block copolymer comprising a polyethylene glycol and polyaspartic acid or polygutamic acid:

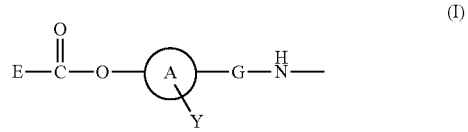

wherein A represents a monocyclic or fused aromatic group; G represents a (C1-C6) alkylene group which may be substituted; Y represents a hydrogen atom or a substituent; and E represents a residue of methotrexate or pemetrexed.

2. The polymer conjugate of methotrexate or pemetrexed or a pharmacologically acceptable salt thereof according to claim 1, which is represented by the following formula (II):

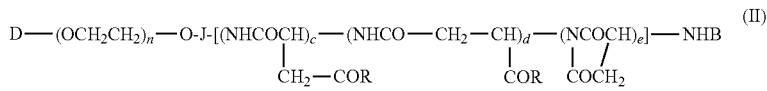
(II)

wherein D represents an unsubstituted (C1-C6) alkyl group; a mean value of n is 50 to 1000; J represents a (C2-C6) alkylene group; a mean value of c+d+e is 5 to 100, while c+d represents an integer; R represents a hydroxy group or the substituent represented by the formula (I), whereas at least one of R in one molecule is the substituent represented by the formula (I); and B represents a (C1-C6) acyl group.

3. The polymer conjugate of methotrexate or pemetrexed or a pharmacologically acceptable salt thereof according to claim 1, wherein the substituent represented by the formula (I) is a substituent represented by the following formula (III):

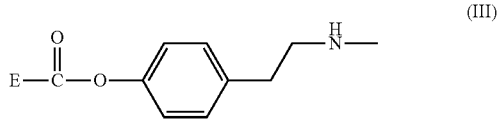
(III)

wherein E represents a residue of methotrexate or pemetrexed.

4. An anticancer drug comprising, as an active ingredient, the polymer conjugate of methotrexate or pemetrexed or a pharmacologically acceptable salt thereof according to claim 1, 2, or 3.

5. A therapeutic drug for inflammatory diseases comprising, as an active ingredient, the polymer conjugate of methotrexate or pemetrexed or a pharmacologically acceptable salt thereof according to claim 1, 2 or 3.

6. The polymer conjugate of methotrexate or pemetrexed of claim 1, wherein a mixture of the α-substituted regioisomer of the substituent of formula (I) linked to said methotrexate or pemetrexed and the γ-substituted regioisomer of the substituent of formula (I) linked to said methotrexate or pemetrexed is bound to said polymer conjugate.

\* \* \* \* \*